United States Patent
Lacerda Junior et al.

(10) Patent No.: US 11,753,361 B2
(45) Date of Patent: Sep. 12, 2023

(54) METHOD OF ISOLATION OF ARN ACIDS FROM NAPHTHENATE DEPOSITS

(71) Applicants: PETROLEO BRASiLEiRO S.A.—PETROBRAS, Rio de Janeiro (BR); UNIVERSIDADE FEDERAL DO ESPIRITO SANTO—UFES, Vitoria (BR)

(72) Inventors: Valdemar Lacerda Junior, Vila Velha (BR); Eliane Valeria De Barros, Vila Velha (BR); Alvaro Cunha Neto, Vitoria (BR); Wanderson Romao, Vitoria (BR); Cristina Maria Dos Santos Sad, Sera (BR); Paulo Roberto Filgueiras, Vitoria (BR); Eustaquio Vinicius Ribeiro De Castro, Vila Velha (BR); Luiz Silvino Chinelatto Junior, Rio de Janeiro (BR); Juliana Navarro Bertelli, Vitoria (BR); Rogerio Mesquita De Carvalho, Rio de Janeiro (BR)

(73) Assignees: PETROLEO BRASILEIRO S.A.-PETROBRAS, Rio de Janeiro (BR); UNIVERSIDADE FEDERAL DO ESPIRITO SANTO-UFES, Vitoria (BR)

( * ) Notice: Subject to any disclaimer, the term of this patent is extended or adjusted under 35 U.S.C. 154(b) by 77 days.

(21) Appl. No.: 17/546,373

(22) Filed: Dec. 9, 2021

(65) Prior Publication Data
US 2022/0177400 A1 Jun. 9, 2022

(51) Int. Cl.
| | | |
|---|---|---|
| C07C 51/02 | (2006.01) | |
| C07C 51/48 | (2006.01) | |
| B01D 15/42 | (2006.01) | |
| B01D 15/36 | (2006.01) | |
| C07C 51/47 | (2006.01) | |

(52) U.S. Cl.
CPC ............ *C07C 51/02* (2013.01); *B01D 15/361* (2013.01); *B01D 15/426* (2013.01); *C07C 51/47* (2013.01); *C07C 51/48* (2013.01)

(58) Field of Classification Search
CPC .... B01D 15/361; B01D 15/426; C07C 51/02; C07C 51/47; C07C 51/48; C07C 2601/08; C07C 53/134
See application file for complete search history.

(56) References Cited

U.S. PATENT DOCUMENTS

| | | |
|---|---|---|
| 8,084,264 B2 | 12/2011 | Marshall et al. |
| 8,674,161 B2 | 3/2014 | Mediaas et al. |
| 9,983,187 B2 | 5/2018 | Albuquerque et al. |
| 2010/0297217 A1* | 11/2010 | Rowland ............... A61P 35/00 560/116 |
| 2012/0330057 A1 | 12/2012 | Levine et al. |
| 2016/0153956 A1 | 6/2016 | Albuquerque et al. |
| 2017/0269042 A1 | 9/2017 | Paek et al. |

FOREIGN PATENT DOCUMENTS

| | | |
|---|---|---|
| BR | PI1011451 B1 | 3/2016 |
| BR | 102014029770 A2 | 5/2016 |
| CN | 103320160 A | 9/2013 |
| CN | 103805227 A | 5/2014 |
| GB | 2447667 A | 9/2008 |
| WO | 2008114015 A2 | 9/2008 |
| WO | 2010151139 A3 | 12/2010 |

OTHER PUBLICATIONS

Nordgard, E.L.; Simon, S.; Sjoblom; J., J. Dispersion Sci. Technol. 33:1083-1092, 2012.
Bertelli, J.N.; Dip, R.M.M.; Pires, R.V.; Albuquerque, F.C.; Lucas, E.F. Energy Fuels, 28, 1726-1733, 2014.
Nichols D.A., Rosario F.F., Bezerra M.C.M., Gorringe S.E., Williams H.L., Graham G.M. Paper No. SPE 169756, 2014.
Juyal, P., Mapolelo M.M., Yen A., Rodgers R.P., Alleson S.J. Energy Fuels, 29, 2342-2350, 2015.
Eke W.I., Victor-Oji C. & Akaranta O. J. Petrol. Explor. Prod. Technol. 10, 805-819 (2020).
Lee, W.; Min, J.; Ahn, YH.; Baek, S.; Koh, C.A.; Lee, J.W. Ind. Eng. Chem. Res. 58, 12, 5064 5070, 2019.
Putmann, J.C.; Marshall, A.G., Energy Fuels, 30 (7), p. 5651 5655, 2016.
Knudesen, A.; Nordgard, E.L.; Diou, O.; Sjoblom, J., J. Dispersion Sci. Technol. 33:1514 1524, 2012.
Mediaas, H.; Grande, K.V.; Hustad, B.M.; Rasch, A.; Rueslatten, H.G.; Vinstad, J.E. Paper No. SPE 80404, 2003.
Lutnaes, B.; Brandal, O.; Sjoblom, J.; Krane, J. Org. Biomol. Chem. 4, 616 620, 2006.
Mapolelo, M.M.; Satanford, L.A.; Rodgers, R.P.; Yen, A.T.; Debord, J.D.; Asomaning, S.; Marshall, A.G., Energy Fuels 23, 349-355, 2009.
Mapolelo, M.M.; Rodgers, R.P.; Blakney, G.T.; Yen, A.T.; Asomaning, S.; Marshall, A.G., Int. J. Mass Spectrom. 300, 149 157, 2011.
Mohammed, M.A. and Sorbie, K.S. Physicochem. Paper No. SPE 121633, 2009.
Simon, S.; Nordgard, E.; Bruheim, P.; Sjoblom, J., J. Chromatogr. A, 1200, 136 143 (2008).

* cited by examiner

*Primary Examiner* — Yevgeny Valenrod
*Assistant Examiner* — Blaine G Doletski
(74) *Attorney, Agent, or Firm* — RAPHAEL BELLUM PLLC

(57) ABSTRACT

The present invention relates to the field of laboratory-scale sample preparation, which describes a methodology for the specific isolation of tetraprotic naphthenic acids, called ARN acids, from residual naphthenate deposits from petroleum production.

The method consists of cleaning the naphthenate deposit, converting the naphthenate salts to naphthenic acids and isolating the ARN acids from the other organic acids, using a silica-based sorbent material with aminopropyl functional groups, previously selected for an efficient elution of different functional groups and polarities.

6 Claims, 7 Drawing Sheets

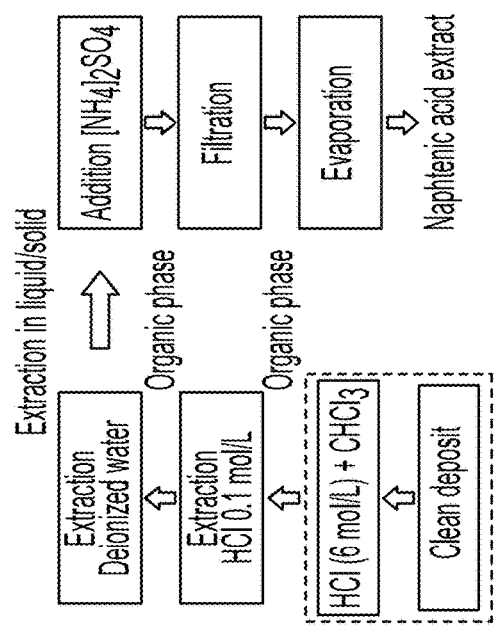
FIG. 1C
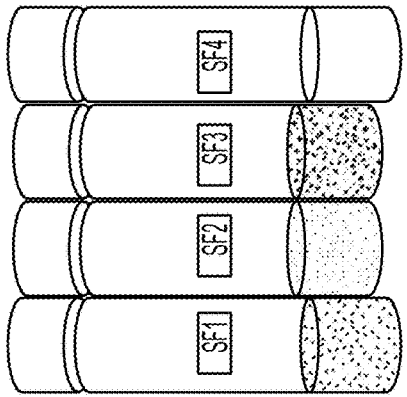
FIG. 1E
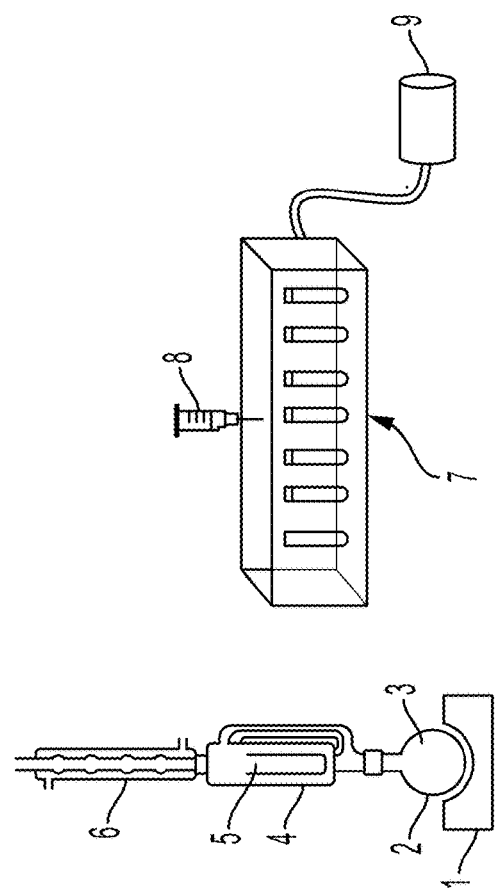
FIG. 1B
FIG. 1A
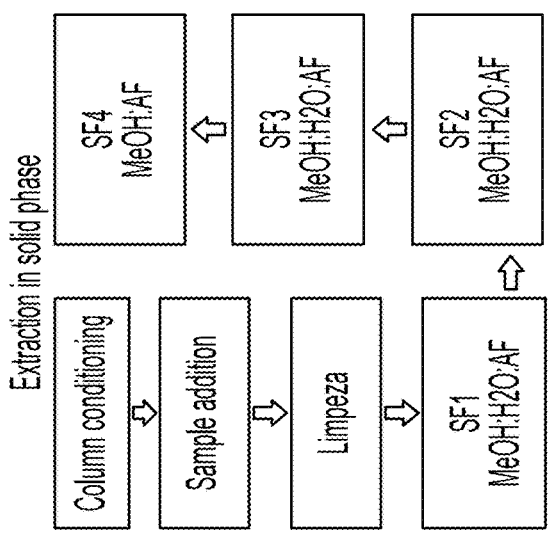
FIG. 1D

METHOD OF ISOLATION OF ARN ACIDS FROM NAPHTHENATE DEPOSITS

FIELD OF THE INVENTION

The present invention relates to the field of method of preparation of laboratory-scale of sample in which it describes a methodology for the specific isolation of tetraprotic naphthenic acids (ARN acids) from residual naphthenate deposits from petroleum production. The method consists of cleaning the naphthenate deposit, converting the naphthenate salts into naphthenic acids and isolating the ARN acids from the other organic acids, using a silica-based sorbent material having aminopropyl functional groups, through a sequence of elutions of different polarities.

BACKGROUND

Naphthenate deposits consist of insoluble salts having polymeric structure, of "tacky" behavior and high interfacial activity formed at the oil/water interface, due to the presence of a specific group of high molecular weight naphthenic acids, sometimes called ARN acids or even $C_{80}$-tetra-acids ($C_{80}$-TA). These acids are provided with four carboxylic terminations (tetraprotic) which impart to these species the ability of performing cross-links with divalent cations (mainly calcium ions) present in water produced in petroleum operations (Nordgard, E. L.; Simon, S.; Sjöblom, J. *J. Dispersion Sci. Technol.* 33:1083-1092, 2012).

It is reported that molecules of ARN acid are not commercially available. Thus, these species are obtained from their source matrix, requiring the application of previous extraction methods (Nordgard, E. L.; Simon, S.; Sjöblom, J. *J. Dispersion Sci. Technol.* 33:1083-1092, 2012).

In document SPE 80404 of the *Society of Petroleum Engineers* (Mediaas et al., 2003) it was developed a methodology for obtaining naphthenic acids from crude oil and other organic solvents by carbohydrate bases ion exchange resin (Acid-IER).

U.S. Pat. No. 8,084,264-B2 (Marshall et al., 2011) describes a methodology of obtaining ARN acids by submitting liquid hydrocarbon samples (including crude oil) to a treatment with gaseous ammonia and the reaction product is aged, recovered and analyzed by mass spectrometry. The method is considered time-consuming and requires temperature control and extra care with gaseous ammonia, which is toxic.

In Chinese patent document CN103805227(A) (Liu Jianchun et al., 2012) propose a method of pre-treating crude oil having high acid content. The method involves several steps comprising submitting crude oil to deacidification, electrodesalination and ending with acidified extraction to separate naphthenic acids, which are recovered by an organic solvent.

The Chinese patent document CN103320160(A) (Tang Zhe et al., 2012) refers to a type of pretreatment method with acid-containing crude oil, desalination by aquathermolysis. During aquathermolysis the acids are recovered from the oil.

In patent documents WO2010/151139-A3 (2010), U.S. Pat. No. 8,674,161-B 2 (2014) and BRPI1011451-B1 (2018), Mediaas et al. propose isolation and quantification of ARN acids in crude oil samples. The process consists of submitting the oil sample to a solid medium for selective absorption/adsorption for ARN acids, which are recovered by an organic solvent and finally quantified by appropriate analytical techniques.

In the Brazilian patents BR102014029770-A2 (2014) and the U.S. Pat. No. 9,983,187-B2 (2018), Albuquerque et al. present a method of extraction and quantification of precursor acids from calcium naphthenate deposits present in crude oil. The system consists of using a column having granular solids (diatomaceous earth, for example) and calcium buffering agents. ARN acids are regenerated by the addition of an acid in an organic solvent which are rotoevaporated and quantified by appropriate analytical techniques.

In the US2017/0269042-A1 (Paek et al., 2017) describe the use of a quaternary amine-based ion exchange resin and a sequence of solvents and solvent mixtures for obtaining ARN acids in crude oil samples.

ARN acids are reported to occur at low concentration (0.6-3.6 ppm) in crude oil, but they are predominant in calcium naphthenate deposits (NICHOLS D. A., ROSARIO F. F., BEZERRA M. C. M., GORRINGE S. E., WILLIAMS H. L., GRAHAM G. M. Paper No. SPE 169756, 2014; Juyal, P., Mapolelo M. M., Yen A., Rodgers R. P., Alleson S. J. Energy Fuels, 29, 2342-2350, 2015; and emphasized by EKE W. I., VICTOR-all C. & AKARANTA O. *J. Petrol. Explor. Prod. Technol.* 10, 805-819, 2020), which justifies the obtainment of ARN acids from naphthenate deposits, which are considered residues, arising from petroleum production.

Obtaining ARN acids from calcium naphthenate deposits is not only advantageous in terms of the potential for reusing waste, which is a relevant environmental liability due to reducing environmental damage, but also to avoid release of naphthenic acids, especially ARN acids, to the environment and migration to some watercourse.

Despite related publications, it is highlighted that documents U.S. Pat. No. 8,084,264-B2, CN103805227(A), CN103320160(A), U.S. Pat. No. 8,674,161-B2, BRP-11011451-B1, BR102014029770-A2, US20160153956, U.S. Pat. No. 9,983,187-B2 and US2017/0269042-A1, cited above, are restricted to recovery of ARN acids in liquid hydrocarbons and crude oil, therefore, they are not intended to obtain ARN acids in an adequate quantity and degree of purity for studies on a laboratory scale, among other applications, to which we can mention: (i) preparation of liposomes to produce drugs and other active agents to human and animal individuals (WO 2008/114,015-A2, GB2447667A); (ii) production of hydrate inhibiting surfactants (LEE, W.; MIN, J.; AHN, YH.; BAEK, S.; KOH, C. A.; LEE, J. W. *Ind. Eng. Chem. Res.* 58, 12, 5064 5070, 2019); (iii) template molecule for printing on molecular polymers that could be useful for quantifying and recovering ARN acids from crude oil (PUTMANN, J. C.; MARSHALL, A. G. *Energy Fuels,* 30 (7), p. 5651 5655, 2016); (iv) predictive quantification models; (v) predictive simulation models to evaluate the behavior of these acids in oil-water interface systems with a view to the process of mitigation, prevention, prediction of deposit formation, and (vi) influence of inhibitors for the formation of deposits. calcium naphthenate (KNUDESEN, A.; NORDGARD, E. L.; DIOU, O.; SJÖBLOM, J. *J. Dispersion Technol.* 33:1514 1524, 2012), etc.

Although the method mentioned above, proposed by Mediaas et al. (SPE 80404, 2003) includes to obtain ARN acids from calcium naphthenate deposits, the procedure is considered laborious, requires a significant consumption of solvent and the product obtained remains contaminated with other constituents (Nordgard, E. L.; Simon, S.; Sjöblom, J. *J. Dispersion Sci. Technol.* 33:1083-1092, 2012).

Conventionally, ARN acids are obtained from calcium naphthenate deposits, by acidified extraction, which consists of subjecting the naphthenate salt to an aqueous acid treatment and organic solvent extraction (MEDIAAS, H.;

GRANDE, K. V.; HUSTAD, B. M.; RASCH, A.; RUESLÅTTEN, H. G.; VINDSTAD, J. E. Paper No. SPE 80404, 2003; BERTELLI, J. N.; DIP, R. M. M.; PIRES, R. V.; ALBUQUERQUE, F. C.; LUCAS, E. F. *Energy Fuels,* 28, 1726-1735, 2014). In this procedure, it is important that the volumetric ratio between the two solutions is sufficient for the naphthenate salts to convert into free acids dissolved in the organic phase, leaving the counterions in the aqueous phase (BRAN DAL, 0.; SJÖBLOM, J.; KRANE, *J. Org. Biomol. Chem.* 4, 616 620, 2006). From this step, the acids can be recovered by drying under a nitrogen stream (MAPOLELO, M. M.; SATANFORD, L. A.; RODGERS, R. P.; YEN, A. T.; DEBORD, J. D.; ASOMANING, S.; MARSHALL, A. G. *Energy Fuels,* 23, 349-355, 2009; MAPOLELO, M. M.; RODGERS, R. P.; BLAKNEY, G. T.; YEN, A. T.; ASOMANING, S.; MARSHALL, A. G. *Int. J. Mass Spectrom.* 300, 149 157, 2011; JUYAL, P.; MAPOLELO, M. M.; YEN, A.; RODGERS, R. P.; ALLESON, S. *J. Energy Fuels,* 29, 2342-2350, 2015) by filtration and rotoevaporation of the solvent under temperature control (MOHAMMED, M. A AND SORBIE, K. S. Paper No. SPE 121633, 2009; MOHAMMED, M. A. AND SORBIE, K. S. Physicochem. Paper No. SPE 121633, 2009b) or by filtration and evaporation of the solvent at room temperature (US2012/0330057A1, 2012; BERTELLI, J. N.; DIP, R. M. M.; PIRES, R. V.; ALBUQUERQUE, F. C.; LUCAS, E. F. *Energy Fuels,* 28, 1726-1735, 2014). However, these procedures do not always provide satisfactory purity for ARN acids, since starting from the same naphthenic deposit, the ARN acid content may vary from one extraction to another. This is because other constituents, especially other types of naphthenic acids, may be present in the oil that originated the deposit (Nordgard, E. L.; Simon, S.; Sjöblom, J. *J. Dispersion Sci. Technol.* 33:1083-1092, 2012).

On the other hand, Simon et al. 2008 (SIMON, S.; NORDGARD, E.; BRUHEIM, P.; SJÖBLOM, J. *J. Chromatogr. A,* 1200, 136 143, 2008) described a procedure for determining the ARN acid content in calcium naphthenate deposits using a quaternary amine-based ion exchange resin. It is noteworthy that this material has drawbacks because it is considered a strong ion exchanger that can make the elution step difficult because it undesirably retains strongly acidic groups. The process is still considered laborious, as it requires several steps, which include acidified extraction, chemical conversion of acids to esters, which limits the process to liquid chromatography technique with ultraviolet detection (HPLC-UV).

The publication US2012/0330057-A1 (2012) describes a process for extracting high molecular weight naphthenic acids from calcium naphthenate salt. The methodology uses a method called double solvent, but which maintains the principle of extraction by acidification, conversion of naphthenate salts into acids. However, this method aims to obtain ARN acids on an industrial scale to be applied in processes that do not require high levels of purity.

In view of the isolation methods of ARN presented, it is confirmed the necessity of developing more efficient methods for a better structural elucidation of these acids, from a matrix of naphthenate deposits.

The transformation of naphthenates deposits, formed in production units, in a standard sample of high value-added, imparts economic advantage to waste treatment concept. Being a differential to chemical synthesis processes to produce standard ARN acid molecules and also other naphthenic acids of smaller molecular weights that may be present in the deposit. The process described here is innovative because it can add value to waste materials from the oil production and exploration process.

In this sense, we propose a new methodology for specific isolation of ARN acids from deposits of naphthenates from oil production. The process consists of cleaning the naphthenate deposit, converting naphthenate salts to naphthenic acids and isolating ARN acids from other organic acids, using a silica-based sorbent material with aminopropyl functional groups, upon a sequence of elutions of different polarities.

The results of ESI(−)-FT-ICR MS showed that the methodology is promising because it provided an excellent separation by difference in polarity and as a function of different molecular weight ranges, thus reducing the complexity of the organic acid extract obtained from the naphthenate deposit. Furthermore, it allowed the separation of the different acidic species that were present in the sample. The results of ESI(−)-FT-ICR MS also indicated that one of the fractions concentrated into ARN acids, including discharged species and especially ARN acids in the form of mono-charged ions. The ESI(−)-Orbitrap MS data corroborated those obtained by ES(−)-FT-ICR MS, making consistent the statement that the extract obtained from the naphthenate deposit contains a mixture of acids and that the fractionation developed provided the isolation of ARN acids from naphthenate deposits. Furthermore, the integrations of the $^1$H NMR spectra of acidic fractions as a function of molecular weight highlighted the expressive presence of alkyl compounds and absence of aromatic hydrogens in the fraction of interest.

SUMMARY OF THE INVENTION

The present document presents a specific method for isolating ARN acids from other naphthenic acids that may be in naphthenate deposits from petroleum production.

The process comprises the following steps: (i) cleaning the deposit; (ii) converting naphthenate salts to naphthenic acids and; (iii) isolating ARN acids from other organic acids, upon a sequence of elutions, using a silica-based sorbent material with aminopropyl functional groups, specifically designed to interact with acidic species.

BRIEF DESCRIPTION OF THE DRAWINGS

The embodiment of the invention can be better explained and understood by reference to the attached drawings, in a schematic and non-limiting way to the inventive scope, and the following description:

FIG. 1A attached shows the naphthenate deposit cleaning system, which is comprised of: (1) heating blanket, (2) borosilicate glass, round-bottomed balloon with short neck, (3) organic solvent to remove residual oil, (4) borosilicate glass Soxhlet extractor, (5) borosilicate glass extraction and reflux tube (6) borosilicate glass Allin cake condenser.

FIG. 1B attached shows the solid phase extraction system consisting of (7) manifold system (it must be more specific), (8) solid phase extraction cartridge with silica-based sorbent material with aminopropyl functional groups and (9) air pump.

FIG. 1C attached shows the process of obtaining the extraction of organic acids by liquid/solid extraction.

FIG. 1D attached presents the sequence of elutions for the specific isolation of ARN acids from other naphthenic acids, present in the extract recovered from the acidification of the naphthenate deposit.

FIG. 1E shows the main acidic sub moieties (SF1-SF4) obtained in the sequence of elutions.

DETAILED DESCRIPTION

Figure 2:
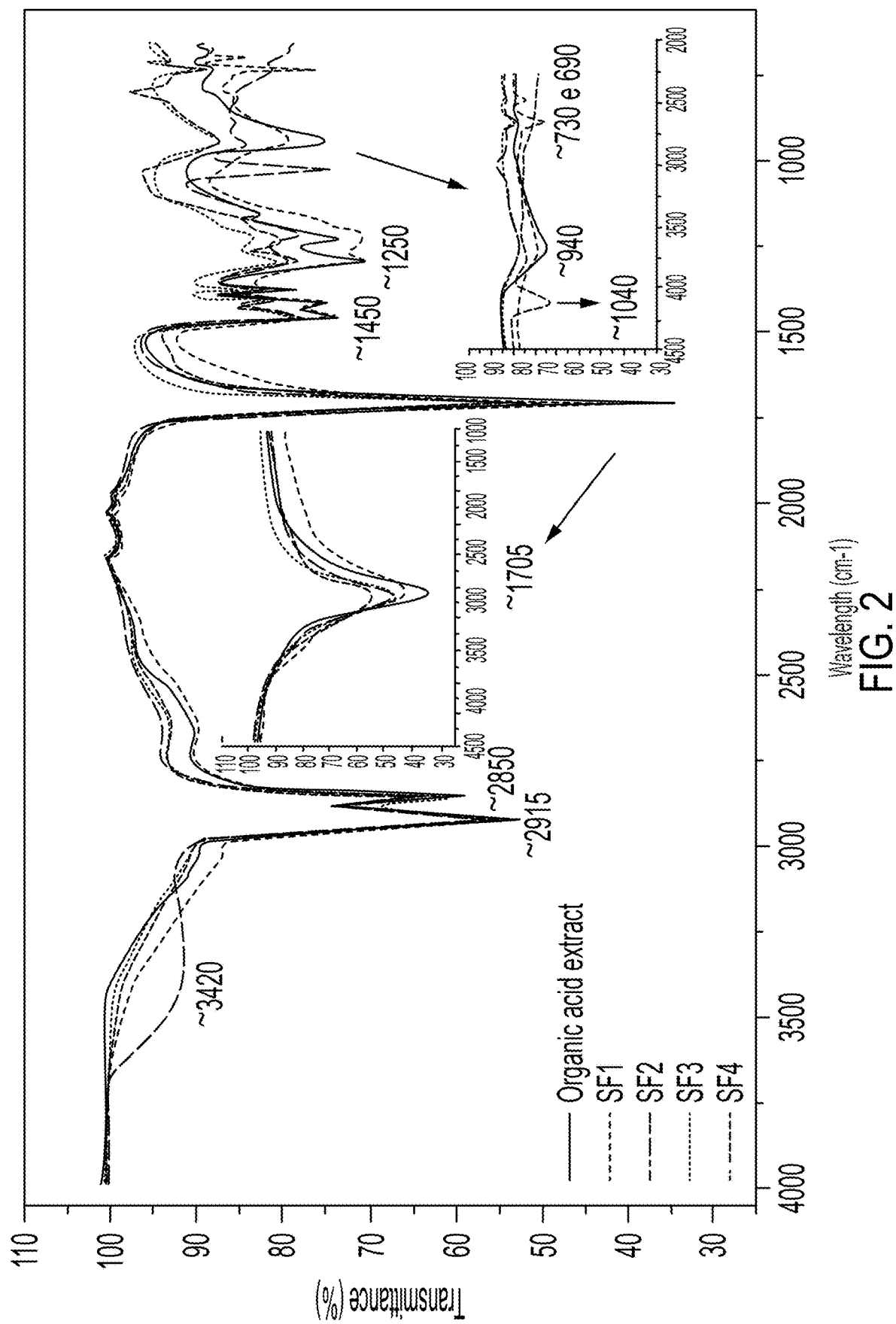
FIG. 2 attached shows the FT-IR spectra of the acid extract recovered from the acidification of the naphthenate deposit and its main sub moieties (SF1-SF4).

The present document shows a specific method for isolating ARN acids from other naphthenic acids that may be in naphthenate deposits from oil production.

The process comprises three steps: (i) cleaning the naphthenate deposit, submitting the deposit to an organic solvent to remove residual oil. In this step, the deposit is washed with an organic solvent, or a sequence of solvents repeated several times until the solvent color remains constant and clear. Here the suggested solvents are toluene, methylene chloride, methanol or any other light hydrocarbon capable of solubilizing the crude oil for its removal.

(ii) conversion of naphthenate salts to acids exposing the clean deposit to an aqueous acid and an organic solvent for the conversion of naphthenate salts to naphthenic acids. The solutions can be mixed directly into the deposit, such as sequentially where the acidic solution is first mixed into the deposit and then the acids are recovered by extraction with the organic solvent. It is important that the volumetric ratio between the two solutions is sufficient so that the free acid monomers remain dissolved in the organic phase (acid extract), leaving the counterions in the aqueous phase. Here the suggested acids are acetic acid, hydrochloric acid, nitric acid or phosphoric acid and possible organic solvents toluene, methylene chloride or any other light hydrocarbon capable of solubilizing and recovering the extracted acids.

(iii) the isolation of ARN acids occurs through an ion-exchange mechanism, which occurs exposing the acid extract to a silica-based sorbent material with aminopropyl functional groups. Importantly, the material works very well in retaining polar ions and separating structural isomers. Silica-based sorbents with aminopropyl functional groups are weaker ion exchangers than quaternary amine sorbents and are ideal for interacting with strongly acidic analytes or with multiple acidic groups. In addition, silica-based sorbent material with aminopropyl functional groups can be found commercially in one or more aspects and can be applied as the filling of a solid phase extraction column.

The sequence of elutions by polarity difference, FIG. 1D, wherein the first three initial steps refer to column preparation and sample introduction: (i) conditioning the column with 5-50 mL of methylene chloride; (ii) addition of the sample, which consists of acid extract (100-600 mg) dissolved in approximately (10-30 mL) methylene chloride; (iii) 5-20 minutes break for column activation.

The next four elutions refer to the cleaning step and the removal of neutral and moderately acidic species, which are not part of the scope: (iv) elution of 10-50 mL with methylene chloride; (v) elution with 10-50 ml methylene chloride and methanol solution (1:1 v/v); elution with 10-50 mL methanol; (vii) elution with 10-50 mL of methanol and water solution (70:30 v/v).

The separation of naphthenic acids according to the different molecular weight ranges occurs in the next four elutions, and consequently enables the isolation of ARN acids: (viii) elution with 10-50 mL methanol, water and formic acid solution (70:30:5 v/v); (ix) elution with 10-50 mL methanol, water and formic acid solution (80:20:5 v/v); (x) elution with 10-50 mL methanol, water and formic acid solution (90:10:5 v/v) and; (xi) elution with 10-50 mL methanol and formic acid solution (100:5 v/v).

The four eluates obtained, in steps viii, ix, x and xi, correspond to the acidic sub moieties, successfully separated as a function of molecular weight, which comprised the extract of acids recovered from the calcium naphthenate deposit. Of these, it is in the fourth sub moiety (xi) that ARN acids are safely concentrated.

To obtain a concentrated sample, the eluate can be further evaporated for solvent removal and acid recovery.

EXAMPLES

Example 1—Investigation of Acidic Species Present in a Calcium Naphthenate Deposit The novel methodology for the isolation of ARN acids by separating naphthenic acids from calcium naphthenate deposits allowed the following results to be achieved.

The cleaning of the deposit was carried out with the aid of a Soxhlet coupled to a condenser (FIG. 1A), under repeated washes with toluene and dichloromethane, resulted in a mass of approximately 4.1 g of clean, dry deposit (~20% m/m recovery). And from that clean deposit mass, 1.9 g of organic acid extract were obtained, which corresponds to a yield close to 47.7% m/m.

The organic acid extract was subjected to solid phase extraction, using a manifold and a commercial ion exchange column Mega Bond Elut-NH2 (2 g×12 mL, Agilent Technologies, USA) supplied by Agilent), as shown in FIG. 1B, producing four main acidic sub moieties (SF1-SF4) obtained from the elution sequence, FIG. 1E.

The FT-IR spectra (FIG. 2) revealed important and common signs to the sub moieties, which were attributed to the major presence of carboxylic acids, revealed by intense bands close to 1,705 cm$^{-1}$ referring to elongations of linkages C=O and bands in 2,915, 2,850 and 1,450 cm$^{-1}$ attributed to C—H elongations of C—H groups $CH_2$ and $CH_3$. However, at wavelengths less than 1,500 cm$^{-1}$ attributed to the fingerprint region, fundamental transitions occur with numerous different elongations.

The FTIR spectra of the SF1, SF2 and SF3 moieties reveal a set of bands (940, 730 and 690 cm$^{-1}$) typical of aromatics, which were not observed for the organic acid extract and for the SF4 sub moiety.

The SF4 still differs from the others by the strong and wide band at 3,420 cm$^{-1}$, which indicates a high concentration of acids, and at 1,040 cm$^{-1}$ which are associated with C—O vibrations of carboxyl groups.

Figure 3:
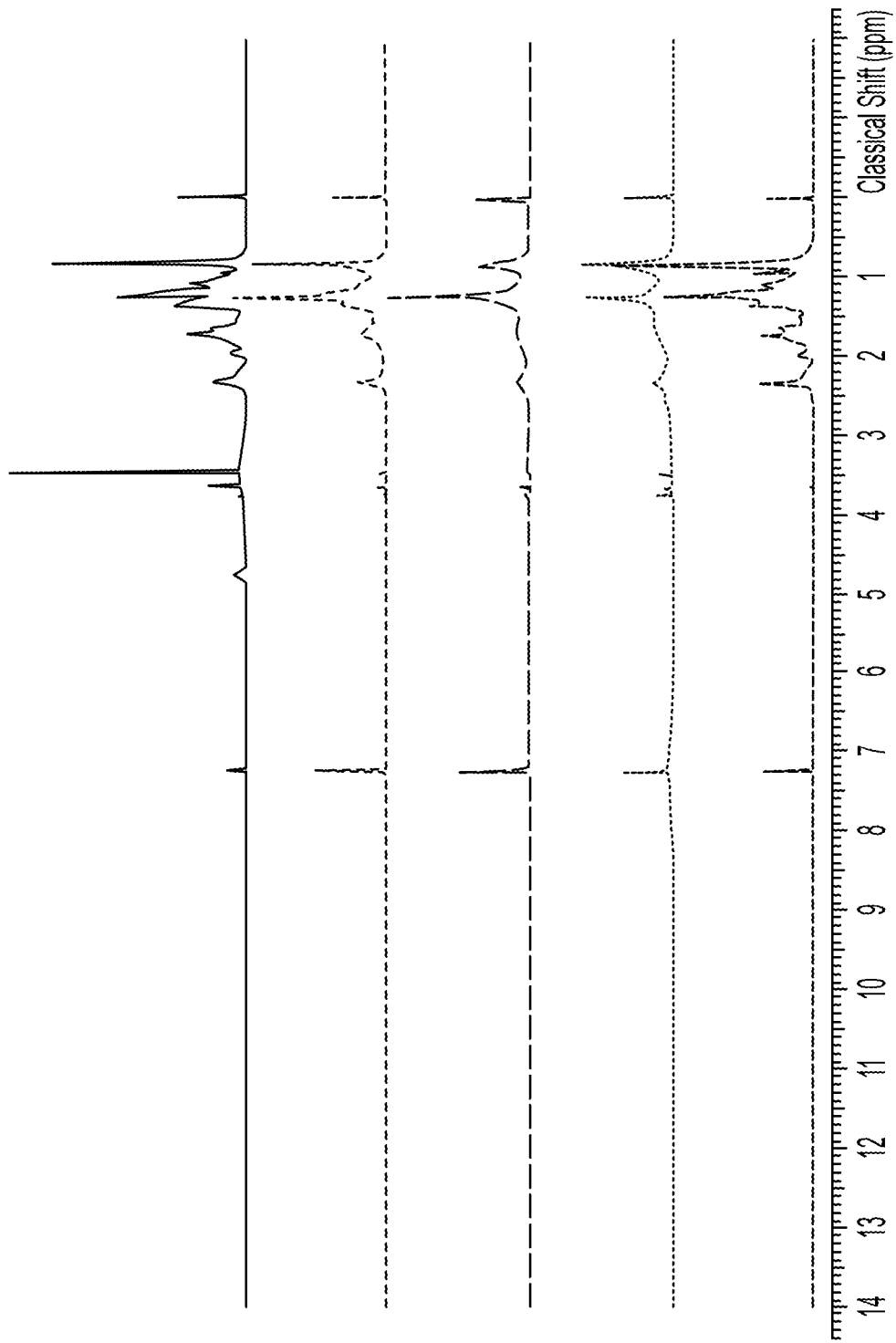
FIG. 3 shows the $^1$H NMR spectra of naphthenic acid extract from calcium naphthenate deposit and its main sub moieties (SF1-SF4). The expansions show signs in the regions between 2.1 and 2.5 ppm, characteristic of hydrogens adjacent to carbonylcarboxylic acids. The inserted structure corresponds to an ARN acid already described by Lutnaes et al. (2006).

$^1$H NMR spectra (FIG. 3) reveal some differences between the spectrum of origin (acid extract or organic extract) and fractionated samples. It is noted that the region of total aliphatic hydrogens (H$_5$), chemical shift (δ) between 0 and 4 ppm, present the greatest number of signals, with emphasis on the region between 0.7 and 1.4 ppm attributed to overlapping of methyl and methylene groups. Signals corresponding to carboxylic acid protons should appear in the range of 10.0 to 14.0 ppm, but hydrogen bonds cause the signal to broaden, making it difficult to visualize and integrate. Such sign was only observed in the organic extract. However, hydrogens adjacent to carboxyl of carboxylic acids can be identified by signs between 2.1 to 2.5 ppm.

The structural detailing of the aliphatic hydrogens presents in the naphthenic acid extract of its main sub moieties indicated that, in all samples, the aliphatic predominance (with values greater than 88.4% mol for SF1 and greater than 91% mol for the other samples). The results highlight a structural diversity between the samples due to the variation of different hydrogen species, where the major presence of H$_\beta$, in all samples, indicates the existence of branches confirming the complexity of the structures.

The predominance of H$_\delta$ and H$_\gamma$ in the naphthenic acid extract from calcium naphthenate deposit and the SF2 and SF3 sub moieties suggest that the compounds have long chains and greater number of substitutions.

On the other hand, it is possible to observe a higher proportion of H$_\beta$ and H$_\alpha$ in sub moieties SF1 and SF4. However, they differ by the absence of aromatic hydrogens in the SF4 sub moiety, while the SF1 sub moiety has aromatic hydrogen content (11.7% mol) which is higher than the values of the other samples.

These results corroborate the FTIR results, as they indicate that the SF4 sub moiety is different from the others, due to the absence of aromatics and reduced number of substitutions (revealed by the H$_\alpha$ content, 23.2% mol).

Figure 4A:
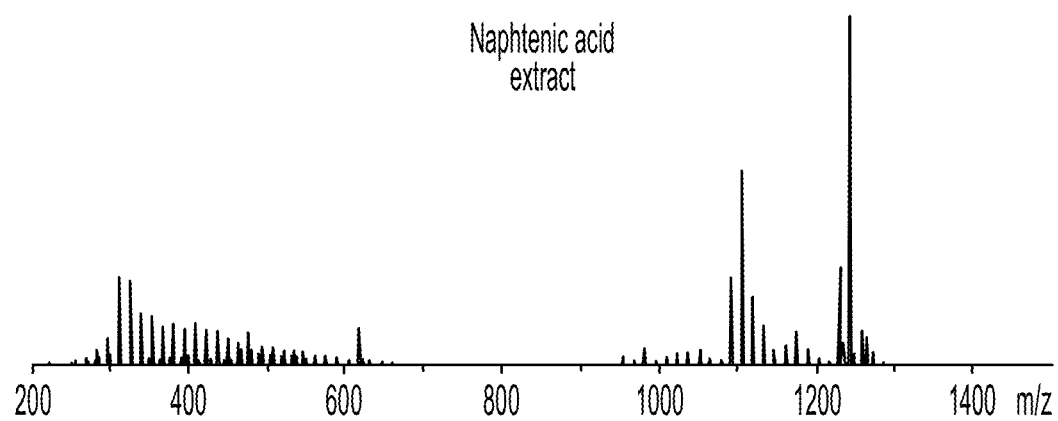
FIG. 4A shows the ESI(-)-FT-ICR MS spectra of acid extract recovered from the acidification of the naphthenate deposit.

The ESI(−)-FT-ICR MS spectra are shown in FIG. 4A. The results reveal that classes O$_4$[H] and O$_8$[H] are predominant in the extract recovered from the acidification of the naphthenate deposit, concentrating in three regions that appeared in the spectrum: (i) with a Gaussian profile of m/z 200-600, attributed to a mixture of compounds with a predominance of class O$_4$[H], which can be attributed to dimer species formed by the self-association of naphthenic acids, which have the same DBE as their constituent monomers (class O$_2$); (ii) with m/z in the range 610-640, attributed to double-charged ions of type [MH]$^{-2}$, ARN$^{-2}$, resulting from the deprotonation of two groups of the four carboxylic groups of the tetraprotic acid that originated it (ARN) and further; (iii) with m/z 950-1,300, attributed to monocharged ions of the type [M-H]$^{-1}$ (ARN$^{-1}$), formed by the deprotonation of only one carboxylic group of the acid of origin.

Figure 4B:
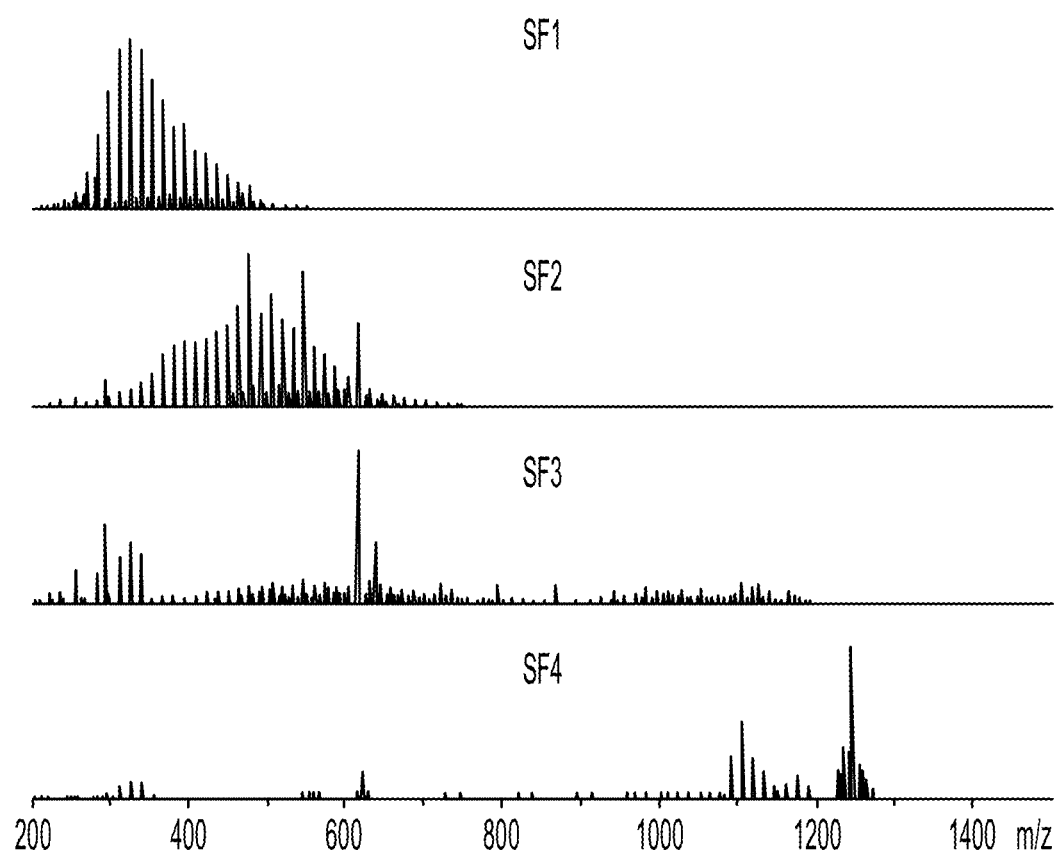
FIG. 4B shows the main sub moieties (SF1-SF4) from FIG. 4A.

FIG. 4B shows the ESI(−)-FT-ICR mass spectra of the sub moieties obtained from the submission of the acid extract, recovered from the acidification of the naphthenate deposit, to the ion exchange resin. It is possible to observe that the first spectra corresponding to the first two sub moieties (SF1 and SF2) presented typical gaussians of naphthenic acids that were separated as a function of their molecular mass. While the SF3 sub moiety presents a gaussian profile referring to a mixture of acids. On the other hand, sub moiety 4 showed a spectrum with predominance of acidic species of higher molecular weight, typical of ARN acids.

The high resolution and mass precision given by ESI(−)-FT-ICR MS provided the detailed identification and differentiation of the species present in the sample. Thus, in the SF4 sub moiety, single charge ions were identified [C$_{81}$H$_{142}$O$_8$—H]$^{-1}$, [C$_{81}$H$_{144}$O$_8$—H]$^{-1}$ and [C$_{71}$H$_{124}$O$_8$—H]$^{-1}$ under the respective m/z 1,242.062480, 1,244.07806 and 1,103.92154, as the most abundant. While the most abundant double charged ions identified were [C$_{81}$H$_{141}$O$_8$-2H]$^{2-}$, [C$_{81}$H$_{143}$O$_8$-2H]$^{2-}$ and [C$_{80}$H$_{141}$O$_8$-2H]$^0$ with m/z 620.52781, 621.53558 and 614.52782, respectively. It was also possible to observe the series of natural tetra-acid, C$_8$, described by Lutnaes et al. (2006).

Detailed acid speciation revealed hydrocarbon skeletons between C$_{65}$ and C$_{76}$ with DBE of 8 and 9 of double charged species. Among the ions of lower molecular weight, it was further identified the double charged ions in SF4 sub moiety [C$_{70}$H$_{122}$O$_8$-2H]$^{2-}$ and [C$_{71}$H$_{124}$O$_8$-2H]$^{2-}$ (m/z 544.44980 and 551.45745) and the monocharged ions [C$_{70}$H$_{122}$O$_8$—H]$^-$, [C$_{71}$H$_{124}$O$_8$—H]$^-$ and [C$_{72}$H$_{126}$O$_8$—H]$^-$ (m/z 1,089.90584, 1,103.92154 and 1,117.93715) to which correspond the homologous series C$_{70}$H$_{121}$O$_8$, C$_{71}$H$_{123}$O$_8$ and C$_{72}$H$_{125}$O$_8$, which was also identified by Juyal et al. (2015) in deposits of calcium naphthenates from oil fields in the South America.

Figure 5:
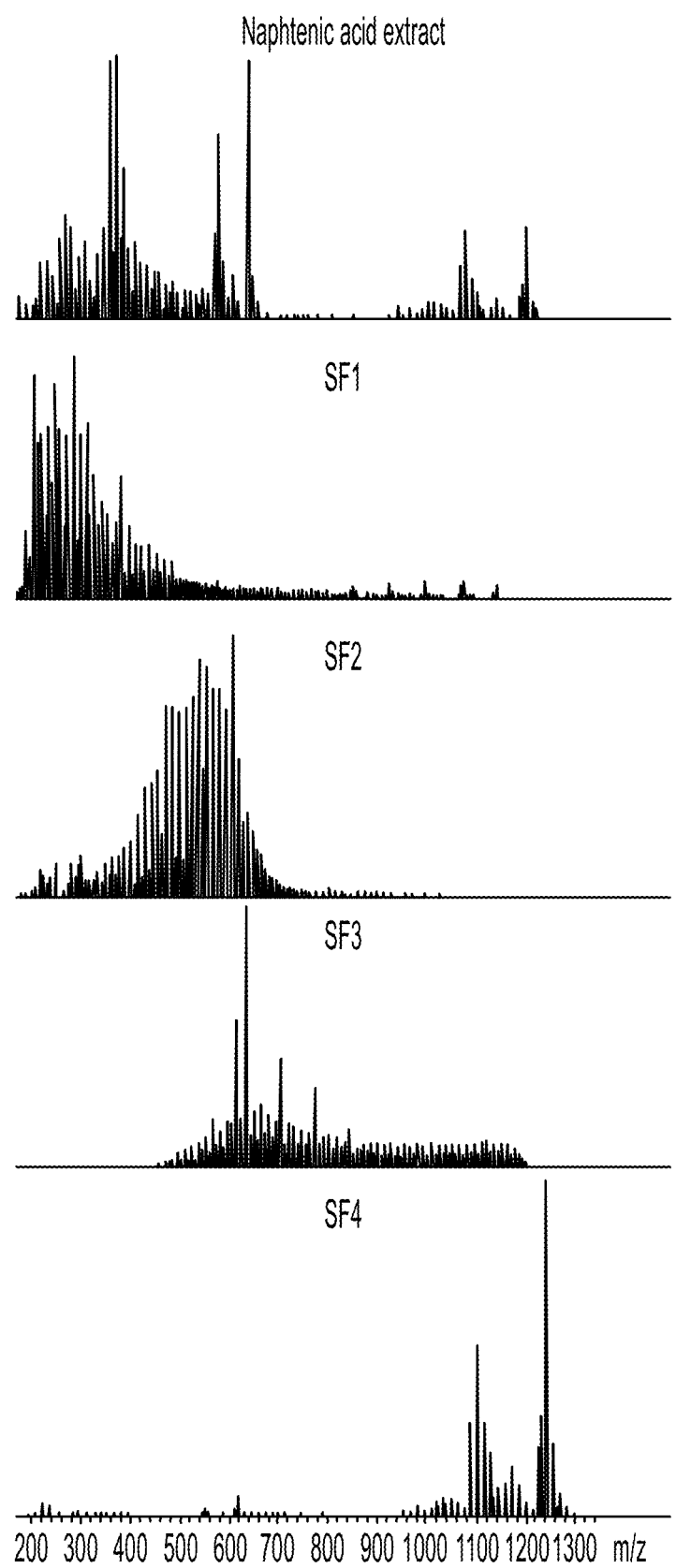
FIG. 5A shows the ESI(-) Orbitrap MS spectra of acid extract recovered from the acidification of the naphthenate deposit.
FIG. 5B shows the main sub moieties (SF1-SF4) from FIG. 5A.

The ESI(−) Orbitrap MS spectra are shown in FIG. 5A and FIG. 5B. Note that the spectral profiles are similar to those obtained by ES(−)-FT-ICR MS, making consistent the statement that the naphthenic acid extract sample from the calcium naphthenate deposit contains a mixture of acids which were separated according to their molecular weight allowing the isolation of ARN acids from naphthenate deposits.

Molecular structures can be related to the number of non-saturations present represented by DBE (number of rings and double bonds), calculated from equation (1) (MCLAFFERTY and TURECEK, 1993):

$$DBE = C - \frac{H}{2} + \frac{N}{2} + 1 \tag{1}$$

where C, H and N represent, respectively, the number of carbons of hydrogen and nitrogen present in the molecular formula of a compound.

Figure 6A:
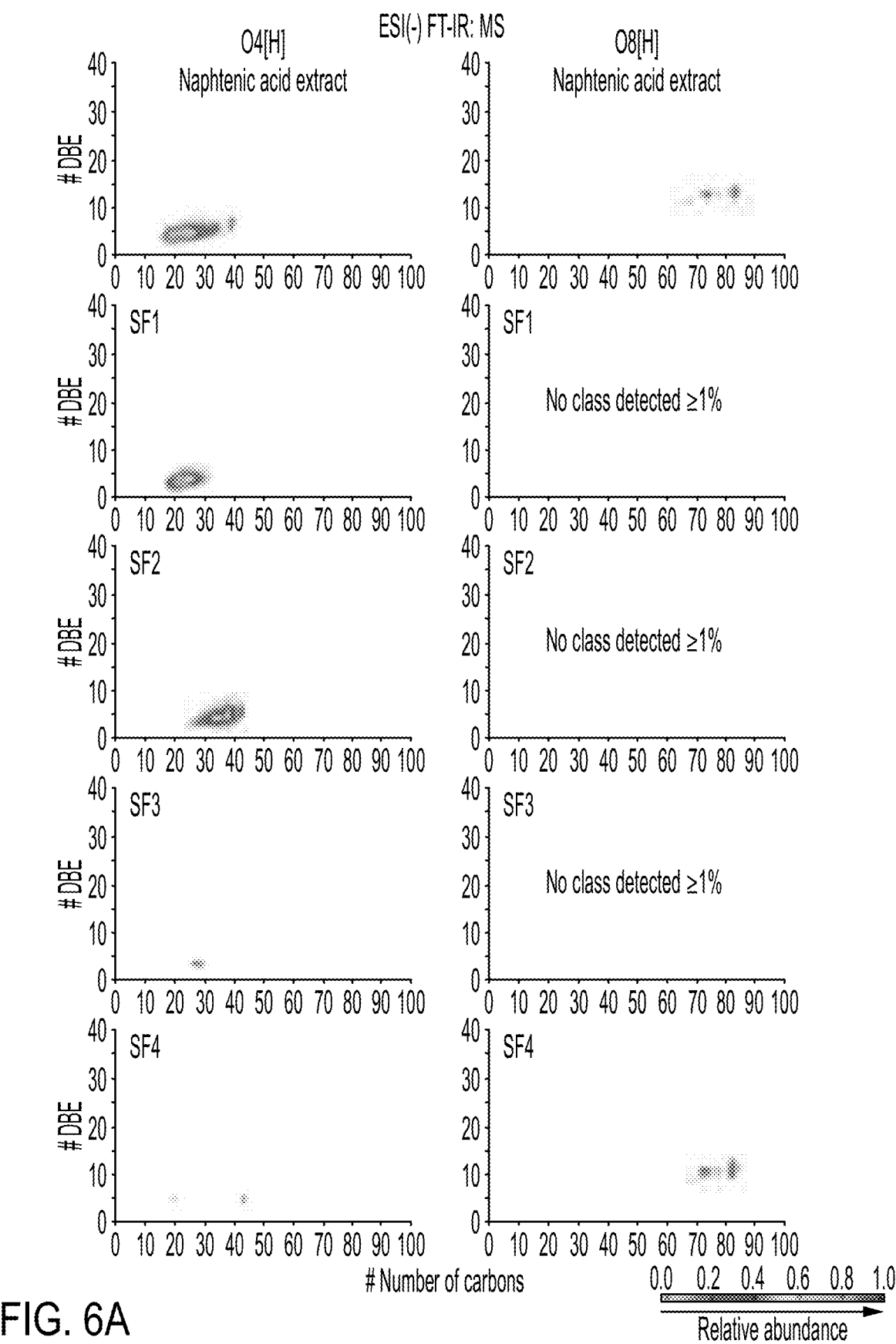
FIG. 6A shows the DBE abundance distribution diagram versus the carbon number (NC) for the highlighted classes ($O_4$[H] and $O_8$[H]) of the extract of acids recovered from the acidification of the naphthenate deposit and its main sub moieties (SF1-SF4) identified by ESI(-)-FT-ICR MS.
Figure 6B:
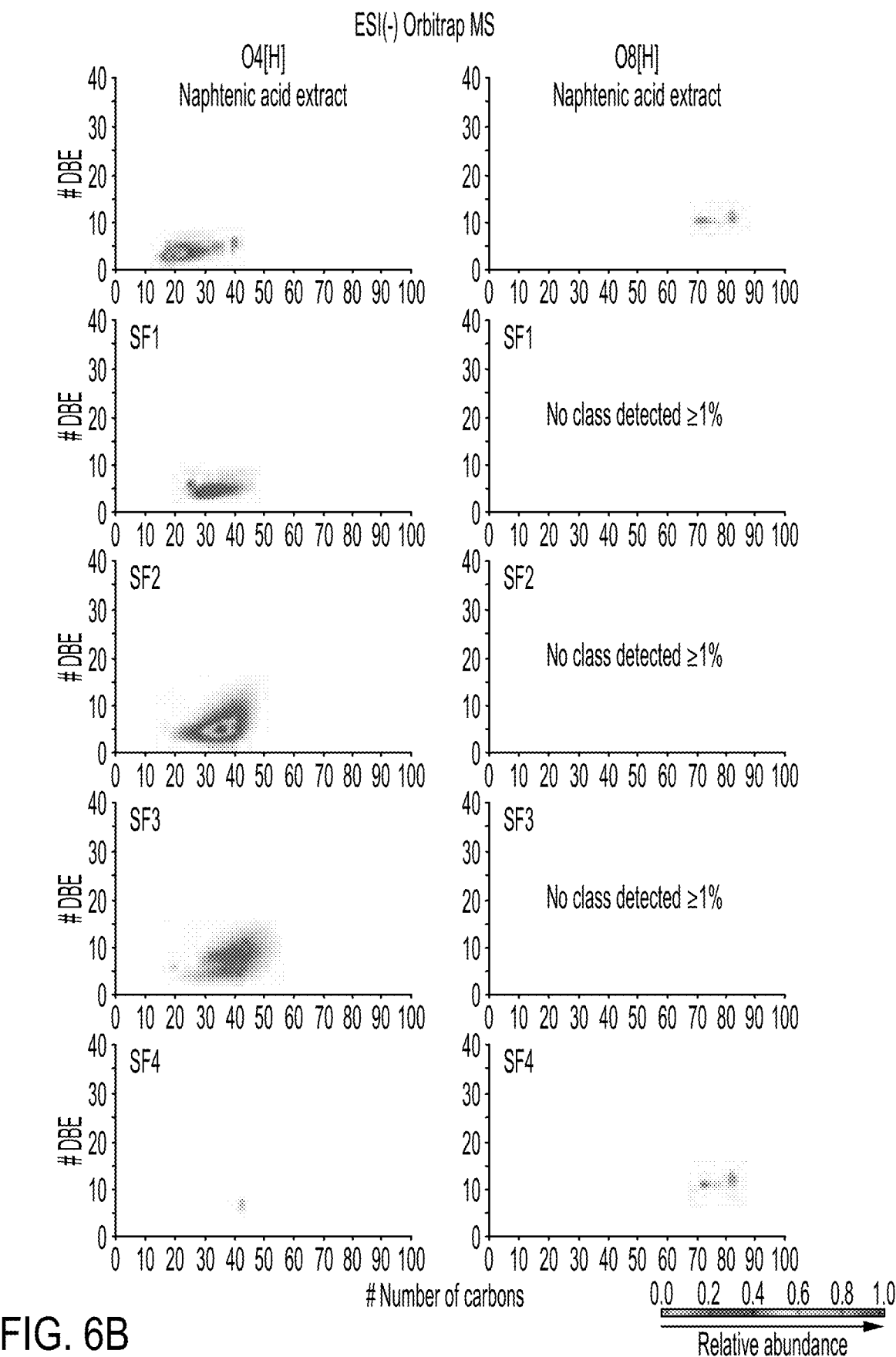
FIG. 6B shows the DBE abundance distribution diagram versus the carbon number (NC) for the highlighted classes ($O_4$[H] and $O_8$[H]) of the extract of acids recovered from the acidification of the naphthenate deposit and its main sub moieties (SF1-SF4) identified by ESI(-) Orbitrap MS.

Thus, there is a significant similarity of the graphs generated between ESI(−)-FT-ICR MS (FIG. 6A) and ESI(−) Orbitrap MS (FIG. 6B).

Note that the first two moieties (SF1 and SF2) have mostly class O$_4$ compounds, the third sub moiety (SF3) concentrates compounds of double charged species, which were even present in three moieties (SF2, SF3 and SF4), such as the ion [C$_{81}$H$_{140}$O$_8$-2H]$^{-2}$ of m/z 620.52758, resulting from the deprotonation of two groups of the four carboxylic groups of the ARN acid that originated it, C$_{81}$H$_{140}$O$_8$. While the fourth sub moiety (SF4), in addition to presenting these recharged species, is highlighted by presenting predominantly long carbon chains (above C$_{70}$) and especially for class O$_8$ (class of ARN acids) with domain for chains with 80 carbons and DBE close to 12.

What is claimed:

1. A method for isolating high molecular weight, tetraprotic naphthenic acids (ARN acids) from naphthenate salt deposits formed during petroleum production, comprising the steps of:
   (i) cleaning the naphthenate salt deposit to remove residual crude oil;
   (ii) converting a portion of the naphthenate salts to naphthenic acids; and
   (iii) isolating the ARN acids from the naphthenic acids, wherein step (iii) comprises using an ion exchange mechanism to isolate the ARN acids from the naphthenic acids by exposing the naphthenic acids to an aminopropyl group-functionalized, silica-based sorbent material; and eluting the ion exchange mechanism with eluents to collect the naphthenic acids in separate eluates according to differences in polarities and as a function of molecular weights, wherein at least one of the eluates comprises ARN acids.

2. The method according to claim 1, wherein the naphthenate deposit is cleaned with an organic solvent in step (i).

3. The method of claim 2, wherein the organic solvent is toluene, dichloromethane, methanol, or a combination thereof.

4. The method according to claim 1, wherein a portion of the naphthenate salts are converted to naphthenic acids by exposing the naphthenic salts to an aqueous acid in step (ii).

5. The method of claim 4, wherein the aqueous acid is acetic acid, hydrochloric acid, nitric acid, phosphoric acids, or a combination thereof.

6. The method of claim 1, wherein the eluent for eluting the eluate comprising ARN acids is 100:5 (v/v) methanol: formic acid.

* * * * *